United States Patent [19]

Cobia et al.

[11] Plant 4,276

[45] Jul. 11, 1978

[54] PIPERACEAE PLANT FAMILY

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 810,650

[22] Filed: Jun. 27, 1977

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Piperaceae Family is related to the *Peperomia rufescens* variety known commercially as 'Red Ripple' and is principally distinguished from this variety and other known related varieties by a growth habit which provides leaf blades that at the upper epidermal side have a basic field which in color is dominated by yellow green and/or greenish yellow hues, which is discontinuous and interrupted along the veins by color that varies in lateral penetration from the vein and is dominated by reddish orange, reddish brown, brown, brownish orange, yellowish brown and/or orange yellow hues, and which is commonly endowed between the primary veins with elongated streaks of color weaknesses that appear as overtones of light greenish gray, grayish white and/or yellowish gray colors; the leaf blades at the lower epidermal side having a basic field which in color is dominated by a yellow green hue, and which is discontinuous and interrupted along the veins by color that varies in lateral penetration from the vein and is dominated by pink and/or red hues.

2 Drawing Figures

The invention relates to a new and distinct variety of the Piperaceae Family and which has been named the *Peperomia rufescens* "Aztec Gold" by the inventors.

There are numerous varieties of the Peperomia genus of the Pepper family found in the market place. The varieties are distinguishable from one another by differences in leaf form, size, hardiness and other characteristics of their growth habits. Among the varieties is the variety known as 'Red Ripple' and which is believed to have been first introduced to the market in the United States in 1972. The 'Red Ripple' variety has a leaf blade with a basic field at the upper epidermal side that can be generally described as dark green in color. The field is discontinuous and brownish coloration appears along the veins of the leaf. The leaf blades are also commonly endowed with color weaknesses between the primary veins and the weaknesses endow the leaf blades with the general appearance of having silver streaks.

A general object of the invention has been to develop a new variety of the Peperomia genus that is similar in appearance to the 'Red Ripple' variety but which is endowed with different color characteristics in the leaf blade. The objectives of the invention have been fully realized by the development of the new plant variety hereinafter described in detail.

The new plant variety was developed in a nursery located at Winter Garden, Fla., and appeared as a vegetative mutation on a plant specimen of the 'Red Ripple' variety that was under cultivation at the mentioned nursery location. The new plant variety was propagated by the inventors at the Winter Garden nursery and has since then been asexually reproduced by the inventors through the propagation of stem cuttings taken from the original plant.

Through successive propagations, it has been ascertained that specimens of the new plant variety generally resemble specimens of the 'Red Ripple' variety but are distinguishable from the parent variety and from other related varieties known to the inventors by a growth habit which is evident in specimens propagated and grown under nursery conditions utilized in the growing of tropical plants at Winter Garden, Fla., as providing leaf blades that 1. at the upper epidermal side have a basic field which in color is dominated by yellow green and/or greenish yellow hues, the basic field being discontinuous and interrupted along the veins by color that varies in lateral penetration from the vein and is dominated by reddish orange, reddish brown, brown, brownish orange, yellowish brown and/or orange yellow hues, and the basic field being commonly endowed with elongated streaks of color weaknesses that appear between the primary veins as overtones of light greenish gray, greenish white and/or yellowish gray colors and 2. at the lower epidermal side have a basic field which in color is dominated by a yellow green hue and which is discontinuous and interrupted along the veins by color that varies in lateral penetration from the vein and is dominated by pink and/or red hues.

The accompanying drawings serve by color photographic means, to illustrate the new plant variety and wherein one sheet contains two color photographs showing potted specimens of the new plant variety with one of the specimens being illustrated in bloom and wherein the second sheet contains two color photographs which respectively illustrate the color characteristics at the upper and lower epidermal sides of the leaf blades.

The following is a detailed description of the new plant variety with colors and hues, unless otherwise clearly indicated by the text through the absence of color notations, being named in accord with the ISCC-NBS Method of Designating Colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md.

The following description is further based on observations in February of well fertilized plants of from 7 to 10 months old as determined from initial propagation and which were grown under 85° F. shaded glasshouse nursery conditions in the Winter Garden, Fla., area and wherein temperatures range from 60° to 85° F. during the winter months and from 75° to 95° F. during the summer months and are ambient during intervening periods.

DETAILED PLANT DESCRIPTION

Name: *Peperomia rufescens* 'Aztec Gold'.

Parentage: A vegetative mutation from the *rufescens* species of the Peperomia genus that is sold commercially as the 'Red Ripple' variety.

Classification:

*Botanic.*—1. Family: Piperaceae (Pepper Family). 2. Genus: Peperomia. 3. Species: rufescens.

*Commercial.*—Foliage plant.

Form: Herbaceous, low growing, erect, caulescent, tropical plant.

Stems:

*General.*—Caulescent and herbaceous.

*Texture.*—Puberulent with near microscopic hairs that are commonly less than 40 microns in length.

*Size.*—1. Diameter: Usually between 1.5 mm. and 15 mm. intermediate the nodes. 2. Internode length: Usually between 3 mm. and 55 mm.

*Shape.*—Terete and commonly having axially oriented grooves or depressions that are circumferentially spaced apart and appear mainly in the apical stem area.

*Color.*—Commonly grayish red (2.5 R 4/6) (2.5 R 5/6) (5 R 4/6) (5 R 5/6) and/or moderate red (near 5 R 4/8) (5 R 5/8). Microscopic examination revealed that stem coloration is composed of the pattern of "reddish" and "greenish" colors with the former color dominating in newer growth and the latter color dominating in older growth.

Leaves:

*General.*—Simple and exstipulate.

*Arrangement.*—Alternate.

*Margins.*—Entire.

*Venation.*—Palmate with veins depressed at the upper epidermal side and protruding at the lower epidermal side.

*Shape.*—Ovate to orbicular and with leaf tips which are mucronate and with bases which are cordate.

*Petiole.*—1. General: Herbaceous and fleshy. 2. Texture: Puberulent with near microscopic hairs. 3. Shape — Semi-circular in transverse section with a groove or depression in the adaxial surface with a slight flair at the petiole attachment to the stem and with a slight thinning taper toward the leaf blade. 4. Size: a. Length — Usually between 15 mm. and 60 mm. for mature leaves. b. Diameter — (intermediate emergence and leaf blade) — Usually between 1.5 mm. and 5 mm. along the major axis and between 0.8 mm. and 4.5 mm. along the minor axis for mature foliage and with the difference between the major and minor axis being usually less than 1 mm. 5. Color: Commonly pale pink (near 5 R 9/2), light pink (near 5 R 8/4), moderate pink (near 5 R 8/4), deep pink (near 2.5 R 6/8) (near 5 R 6/8), dark pink (2.5 R 6/6) (5 R 6/6), light yellowish pink (near 7.5 R 8/4), moderate yellowish pink (near 7.5 R 8/4), dark yellowish pink (7.5 R 6/6), pale yellowish pink (near 10 R 9/2) and/or moderate red (2.5 R 4/8) (near 2.5 R 5/8) (5 R 4/8) (5 R 5/8). Microscopic examination at 10× reveals that the petiole color is derived from a series of reddish and greenish colored longitudinally extending striations that blend together to determine the petiole color.

*Leaf Blade.*—1. General: Herbaceous and fleshy to leathery. 2. Texture: a. Upper epidermis — Puberulent with microscopic hairs. b. Lower epidermis — Puberulent with microscopic hairs. 3. Size: a. Length — Usually between 32 mm. and 100 mm. at maturity. b. Width (Maximum) — Usually between 32 mm. and 100 mm. 4. Color: a. Upper epidermal side — A discontinuous basic field which in color is dominated by yellow green and/or greenish yellow hues, with interruptions in the continuity along the veins by color that varies in lateral penetration from the veins and is dominated by reddish orange, reddish brown, brown, brownish orange, yellowish brown and/or orange yellow hues, and which is commonly endowed with elongated streaks of color weaknesses between the primary veins that appear as overtones of light greenish gray, grayish white and/or yellowish gray color. Commonly vivid greenish yellow (10 Y 8/12), brilliant greenish yellow (near 7.5 Y 8/10) (near 7.5 Y 8/8) (near 10 Y 8/10) (near 10 Y 8/8), strong greenish yellow (near 7.5 Y 8/10) (near 10 Y 8/10) (near 10 Y 8/8) (near 10 Y 7/10), moderate greenish yellow (near 7.5 Y 8/8) (near 10 Y 8/8), light greenish yellow (near 7.5 Y 8/8) (near 10 Y 8/8), brilliant yellow green (2.5 GY 9/8) (2.5 GY 8/10) (2.5 GY 8/8) (near 5 GY 8/8) and/or strong yellow green (2.5 GY 7/8) (2.5 GY 6/8) (5 GY 7/10) (5 GY 7/8) (5 GY 6/8) in the basic field. Commonly dark reddish orange (near 10 R 4/8), grayish reddish orange (2.5 YR 5/6), moderate reddish brown (10 R 4/6), strong brown (2.5 YR 4/6) (2.5 YR 4/8) (5 YR 4/6), light brown (5 YR 5/6) (7.5 YR 5/6) (near 7.5 YR 5/4) (near 7.5 YR 6/6), brownish orange (near 5 YR 5/6) (near 5 YR 5/8), strong yellowish brown (near 7.5 YR 5/6) and/or dark orange yellow (near 7.5 YR 6/6) along the veins. Commonly pale yellow green (2.5 GY 9/2) (near 2.5 GY 8/2) (5 GY 8/2) (near 7.5 GY 8/2) light greenish gray (near 5 GY 8/1) (10 GY 8/1), greenish white (5 GY 9/1) (10 GY 9/1) and/or yellowish gray (10 Y 8/1) in the steaked areas. b. Lower epidermal side — A basic field which in color is dominated by a yellow green hue and which is discontinuous and interrupted along the veins by color that varies in lateral penetration from the veins and is dominated by pink and/or red hues. Commonly pale yellow green (2.5 GY 9/2) (5 GY 9/2) and/or light yellow green (near 2.5 GY 9/6) (2.5 GY 9/4) (2.5 GY 8/4) (5 GY 9/4) in the basic field and deep pink (2.5 R 6/8), dark pink (2.5 R 6/6), moderate red (near 2.5 R 5/10) (2.5 R 5/8) (2.5 R 4/10) (2.5 R 4/8) (5 R 5/10) (5 R 5/8) (5 R 4/10) and/or strong red (5 R 4/12) along the vein.

Infloresence:

*Form.*—Spike.

*Spike.*—1. General: Apical emergence with usually between 1,000 and 5,000 minute blooms per spike. 2. Size: a. Length — Usually between 85 mm. and 150 mm. b. Diameter (intermediate proximal and distal ends)—Usually between 3 mm. and 8 mm. at maturity. 3. Texture: Fleshy. 4. Shape: Elongated and terete. 5. Color: Commonly light yellow green (2.5 GY 8/6) (5 GY 8.6), moderate yellow green (near 2.5 GY 7/6), strong yellow green (near 2.5 GY 7/8) and/or brilliant yellow green (2.5 GY 8/8).

*Flower.*—1. General: Bisexual, hypogynous, sessile, bracteate and apetalous. 2. Texture: Fleshy. 3. Shape: A sessileovoid with bilateral symmetry. 4. Size (excluding bract): Usually between 0.4 mm. and 1 mm. 5. Androecium: a. General — Two stamens with two celled confluent anthers. b. Filament—(1) General: Fleshy and emerging laterally and slightly proximally of the ovary. (2) Shape: Generally terete with a slight lateral flattening. (3) Size: (a) Length — Usually between 0.2 mm. and 0.8 mm. (b) Diameter — Usually between 0.15 mm. and 0.35 mm. c. Anthers — (1) General: Exserted and dorsifixed with extrorse dehiscence. (2) Shape (predehiscence): Oval with an axially oriented depression along the midline. (3) Size (predehiscence): (a) Length — Usually between 0.2 mm. and 0.7 mm. (b) Diameter (maximum) — Usually between 0.1 mm. and 0.3 mm. 6. Gynoecium: a. General — Monopistillate with superior, one-loculed ovary and no style. b. Ovary — (1) General: A solitary ovule, basal orthotropus. (2) Shape: Generally hemispherical. (3) Size: Usually between 0.3 mm. and 0.9 mm. c. Stigma — (1) General: Bilaterally symmetrical with many minute radially oriented lobes. (2) Shape: Capitate. (3) Size: Usually between 0.15 mm. and 0.5 mm. in diameter.

The following is a general description of a specimen of the new plant variety that was propagated from a stem cutting, the description being taken in the month of February at a time when the plant was five and one half (5½) months old.

Stems:

*Number.*—2.

*Length.*—10.1 cm. and 9.5 cm. respectively.

*Number of nodes.*—11 and 7 respectively.

*Diameter.*—Ranges from 4 mm. at the apex to 7 mm. near the base.

*Internode length.*—Varies from 4.5 cm. to 3 mm.

*Color.*—Grayish red (2.5 R 5/6) and moderate red (5 R 5/8).

Leaves:

*Number of nonembryonic leaves.*—17 mature leaves and 4 immature developing leaves.

*Petioles.*—1. Diameter (Intermediate emergence and leaf blade): Ranges from 3 mm. to 5 mm. 2. Length: Ranges from 15 mm. to 41 mm. at maturity. 3. Color: Light pink (near 5 R 8/4) for older petioles and moderate red (5 R 5/8) for younger mature petioles.

*Blades.*—1. Width (Maximum): Varies from 42 mm. to 74 mm. 2. Length: Varies from 40 mm. to 78 mm. at maturity. 3. Color: a. Upper epidermal surface — Light greenish yellow (7.5 Y 8/8), moderate greenish yellow (7.5 Y 8/8), strong greenish yellow (7.5 Y 8/10) (7.5 Y 8/8) (10 Y 8/10), brilliant greenish yellow (7.5 Y 8/10) (7.5 Y 8/8) (10 Y 8/10) and vivid greenish yellow (10 Y 8/12) in basic field with strong brown (5 YR 4/6) (2.5 YR 4/6) along veins, and five longitudinal streaks between the primary veins of greenish white (10 GY 9/1) (5 GY 9/1) and yellowish gray (10 Y 8/1). b. Lower epidermal surface — Pale yellow green (near 2.5 GY 9/2) and light yellow green (2.5 GY 9/4) in basic field and moderate red (5 R 4/10) (near 5 R 5/10) (2.5 R 5/8) and strong red (5 R 4/12) along veins.

The following is a general description of a typical inflorescence that appeared on a plant that was 1 year in age.

Spike:

*Size.*—1. Length: 110 mm. 2. Diameter(Intermediate distal and proximal ends): 5 mm.

*Color.*—Light yellow green (2.5 GY 8/6) (5 GY 8/6).

Flower:

*Number.*—1,760.

*Diameter.*—0.53 mm. (average).

We claim:

1. The new and distinct plant variety of the Piperaceae Family as is described and illustrated and which is primarily distinguished by a growth habit providing specimens with leaf blades that (1) at the upper epidermal side have a basic field which in color is dominated by yellow green and/or greenish yellow hues, the basic field being discontinuous and interrupted along the veins by color that varies in lateral penetration from the vein and is dominated by reddish orange, reddish brown, brown, brownish orange, yellowish brown and/or orange yellow hues, and the basic field being commonly endowed with elongated streaks of color weaknesses that appear between the primary veins as overtones of light greenish gray, greenish white and/or yellowish grey colors and (2) at the lower epidermal side have a basic field which in color is dominated by a yellow green hue and which is discontinuous and interrupted along the veins by color that varies in lateral penetration from the vein and is dominated by pink and/or red hues.

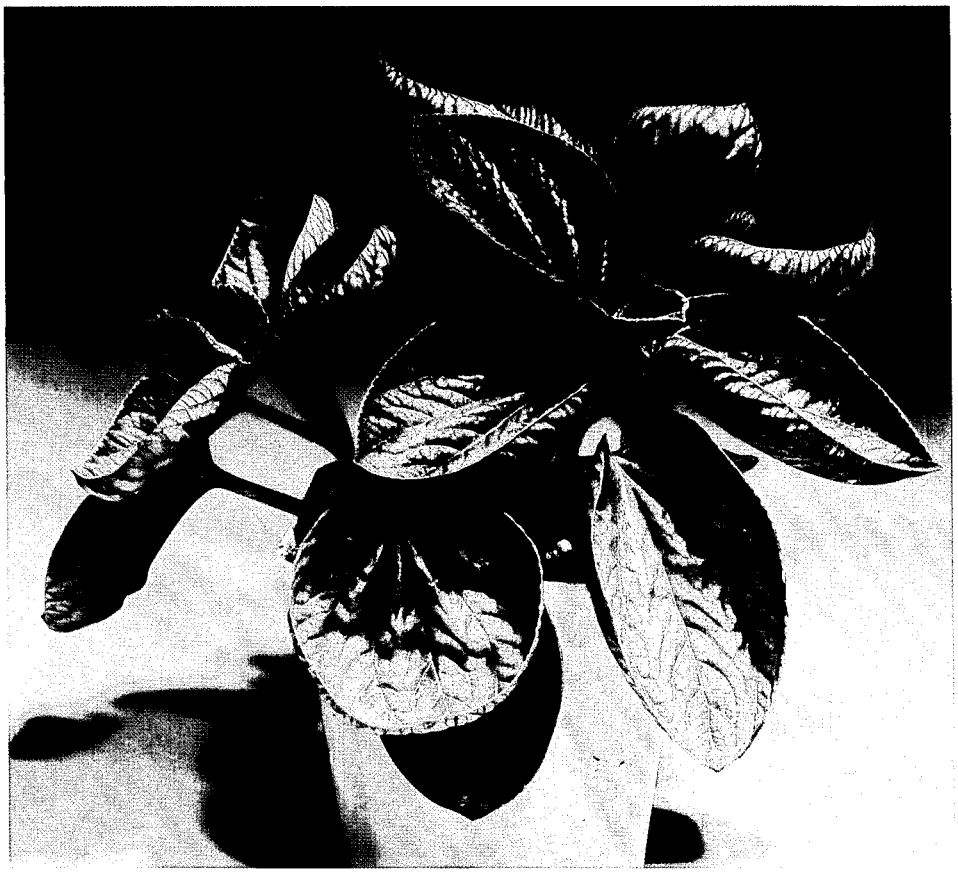
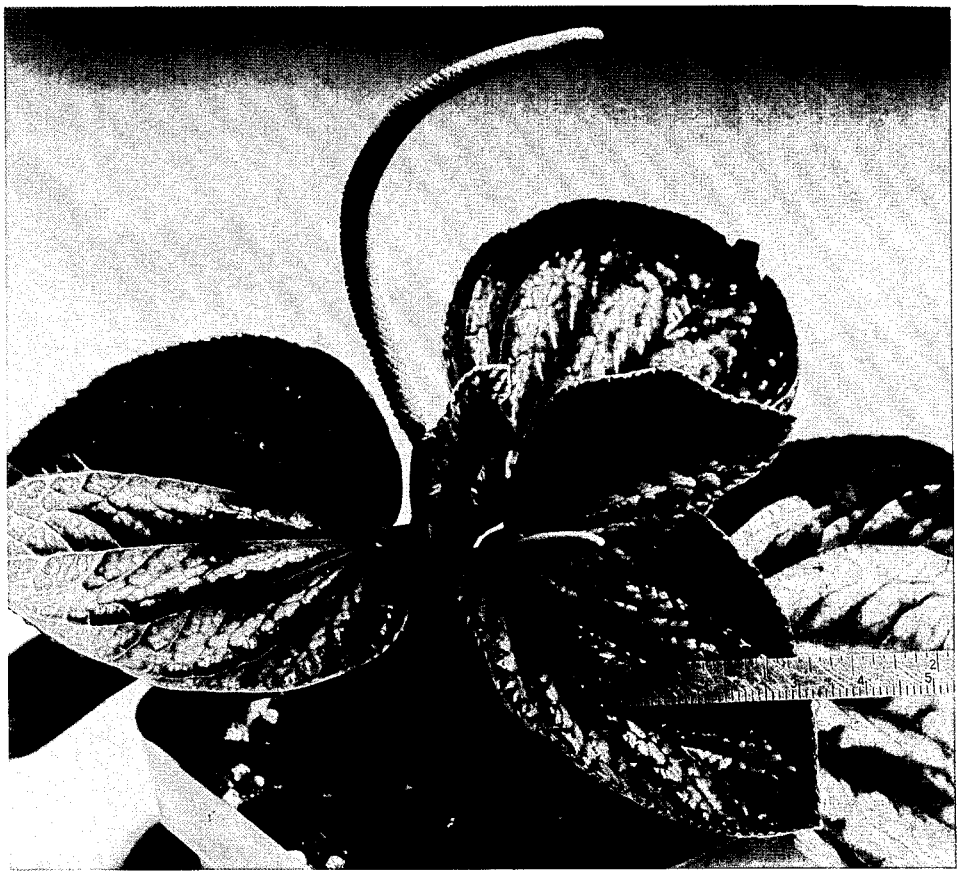

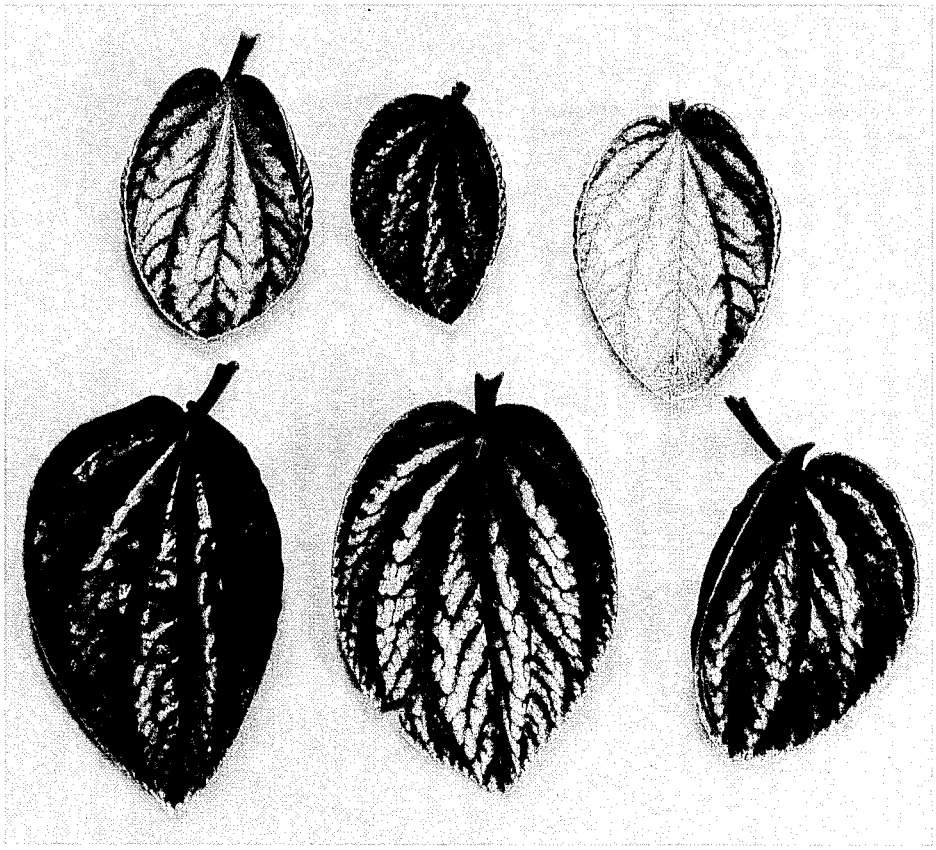
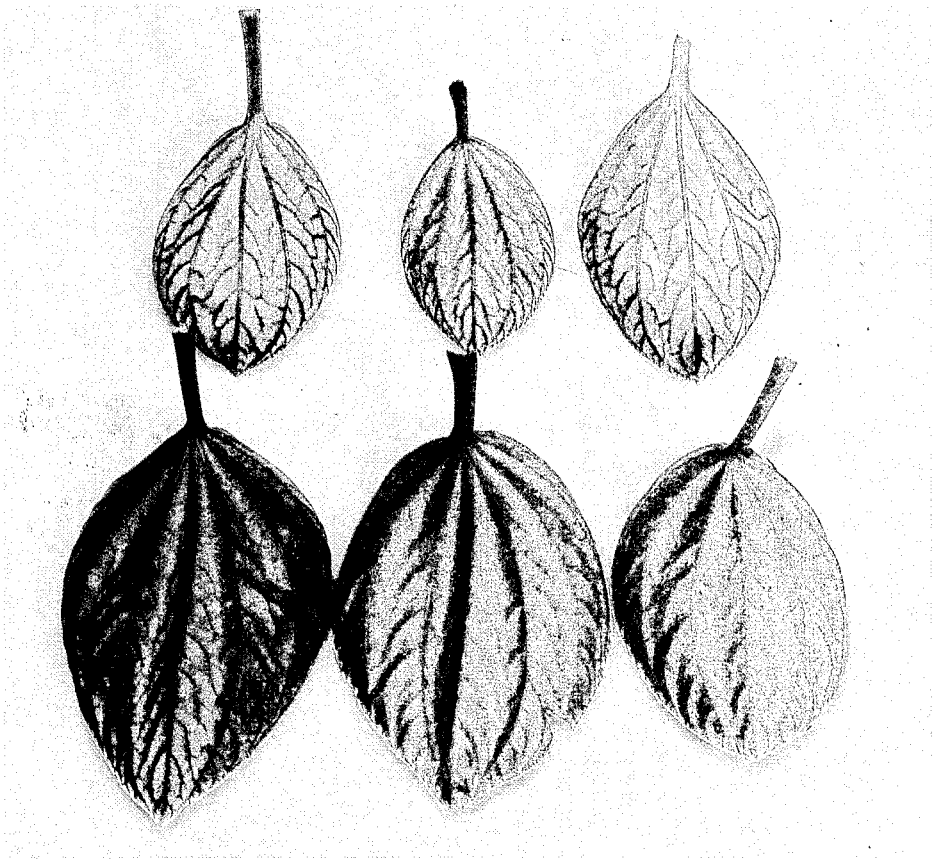

* * * * *